United States Patent [19]
Dorsey

[11] Patent Number: 6,132,447
[45] Date of Patent: *Oct. 17, 2000

[54] UMBILICAL SCISSORS

[76] Inventor: William R. Dorsey, 35 Inverness Ct., Springboro, Ohio 45065

[ * ] Notice: This patent is subject to a terminal disclaimer.

[21] Appl. No.: 09/072,078

[22] Filed: May 4, 1998

Related U.S. Application Data

[62] Division of application No. 08/629,776, Apr. 9, 1996, Pat. No. 5,769,859.

[51] Int. Cl.$^7$ .................................................. A61B 17/32
[52] U.S. Cl. ............................ 606/174; 30/194; 606/167; 606/119
[58] Field of Search .................................... 606/119, 120, 606/137, 167, 174, 205–211; 30/194–262, 346, 52

[56] References Cited

U.S. PATENT DOCUMENTS

| | | |
|---|---|---|
| 4,026,294 | 5/1977 | Mattler . |
| 4,210,148 | 7/1980 | Stivala . |
| 4,428,374 | 1/1984 | Auburn . |
| 4,438,714 | 3/1984 | Smith et al. . |
| 4,572,181 | 2/1986 | Mattler . |
| 4,648,401 | 3/1987 | Mattson . |
| 4,682,598 | 7/1987 | Beraha . |
| 4,870,965 | 10/1989 | Jahanger . |
| 5,009,657 | 4/1991 | Cotey et al. .............................. 606/120 |
| 5,127,915 | 7/1992 | Mattson .................................. 606/120 |
| 5,178,624 | 1/1993 | Kyun ....................................... 606/120 |
| 5,190,556 | 3/1993 | Hessel ..................................... 606/120 |
| 5,281,228 | 1/1994 | Wolfson .................................. 606/120 |
| 5,462,555 | 10/1995 | Bolanos et al. .......................... 606/120 |
| 5,517,761 | 5/1996 | Wang ......................................... 30/254 |

*Primary Examiner*—Glenn K. Dawson
*Attorney, Agent, or Firm*—Jacox, Meckstroth & Jenkins

[57] ABSTRACT

Umbilical scissors having birth-related indicia associated therewith. In this regard, the umbilical scissors may be labeled with the birth data or provided with engraved or embossed birth data or indicia in the form of a color-coded handle to indicate the gender of a baby. Further, birth data may be provided on a label, such as a gummed label or plate, which may be mounted directly to the scissors or to a container or frame in which the scissors are placed for permanent storage and/or display.

10 Claims, 3 Drawing Sheets

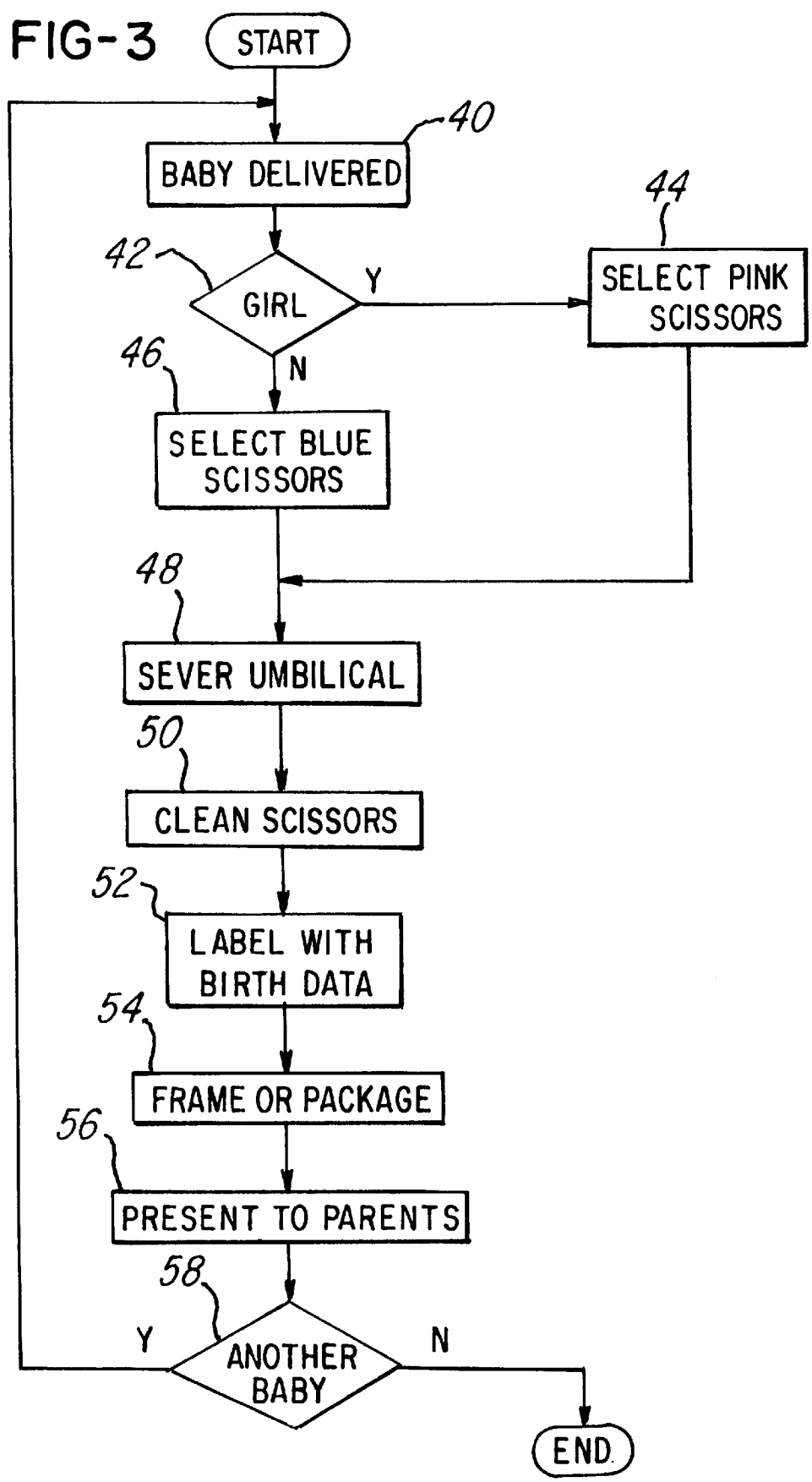

UMBILICAL SCISSORS

CROSS-REFERENCE TO RELATED APPLICATION

This application is a division of Ser. No. 08/629,776 filed Apr. 9, 1996, now U.S. Pat. No. 5,769,859.

BACKGROUND OF THE INVENTION

1. Field of the Invention

This invention relates to umbilical scissors and, more particularly, to customized umbilical scissors having unique birth data or indicia associated therewith to facilitate memorializing and recording the birth data associated with a newborn baby.

2. Description of the Related Art

In the field of obstetrics and during a normal birthing procedure, it is necessary to sever an umbilical cord and separate a baby from its mother. Heretofore, this procedure is normally done with a pair of surgical scissors which are typically stainless steel.

In the past, no method, article or means were provided to utilize the umbilical scissors to memorialize the birthing event and as a means for recording various birthing data.

SUMMARY OF THE INVENTION

Accordingly, it is a primary object of this invention to provide a method and apparatus for memorializing or recording birth data associated with a birth of a baby utilizing umbilical scissors.

Another object of the invention is to provide umbilical scissors which have indicia associated therewith to provide an indication of a baby's gender.

It is another object of the invention to provide a pair of umbilical scissors which have a gender indicia integrally formed as a part of the handle of the scissors.

Another object of the invention is to provide birth data which may be permanently engraved or embossed, for example, on a blade of the scissors or alternatively, permanently recorded on a label which is subsequently situated or placed on the scissors.

In one aspect this invention comprises a method for recording birth data comprising the steps of selecting a pair of gender-indicating scissors based on gender; severing an umbilical cord with said umbilical scissors.

These and other objects and advantages of the invention will be apparent from the following description, the accompanying drawings and the appended claims.

BRIEF DESCRIPTION OF THE DRAWINGS

FIG. 3 is a schematic diagram of a process according to an embodiment of the present invention.

DETAILED DESCRIPTION OF THE INVENTION

Figure 1:
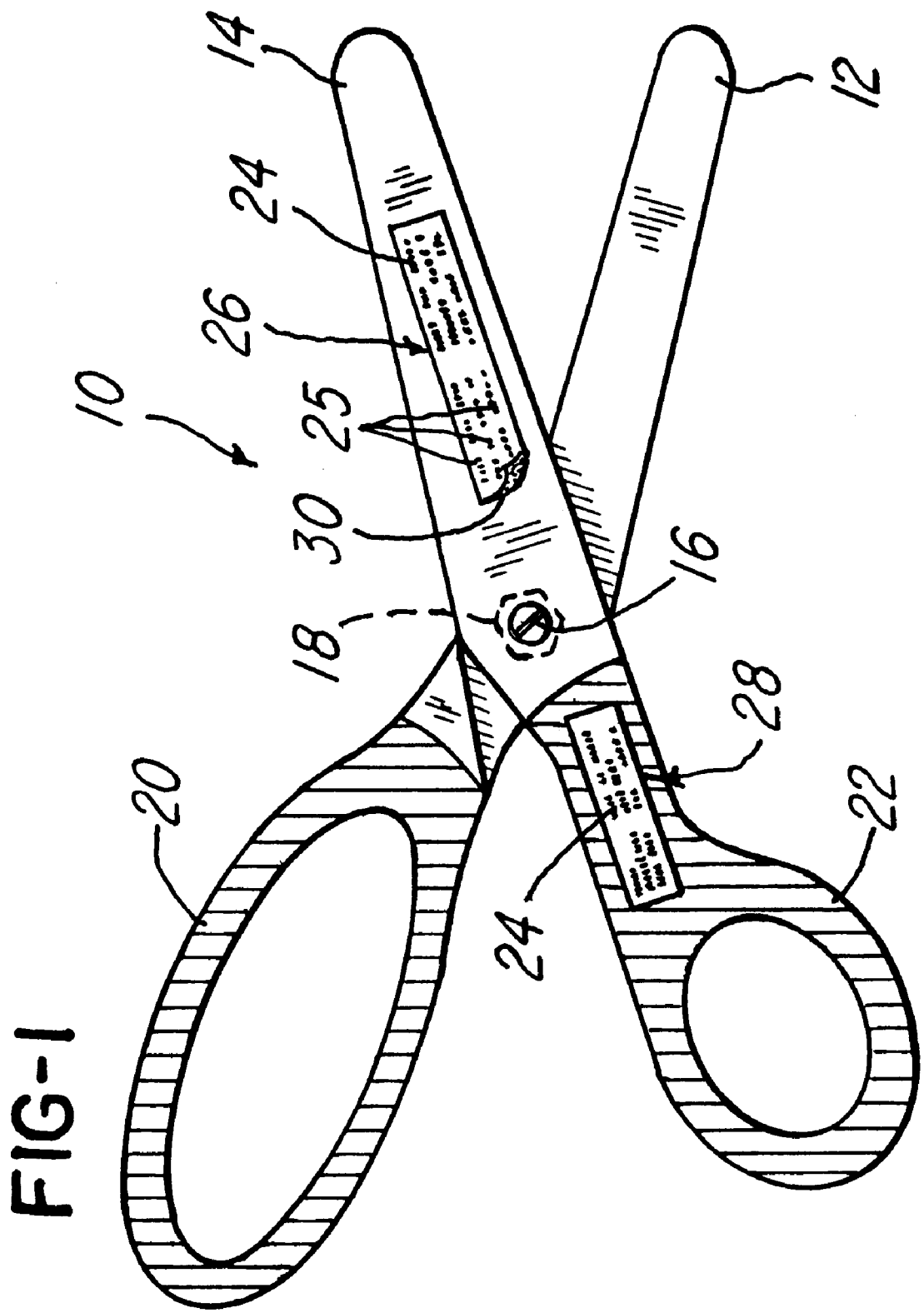
FIG. 1 is a perspective view of a pair of umbilical scissors comprising features of the present invention.

Referring now to FIG. 1, a pair of gender-indicating umbilical scissors 10 are shown. The scissors 10 comprise a first blade or cutting edge 12 and a second blade or cutting edge 14 which are fastened together by a suitable fastener, such as a screw 16 which cooperates with a mating bolt 18 to pivotally secure the first blade 12 to the second blade 14.

In the embodiment being described, the first blade 12 comprises a first handle 20 and the second blade 14 comprises a second handle 22. While the blades 12 and 14 are metal, the handles 20 and 22 may be completely or partially molded from a suitable rubber or plastic material as desired.

Figure 2:
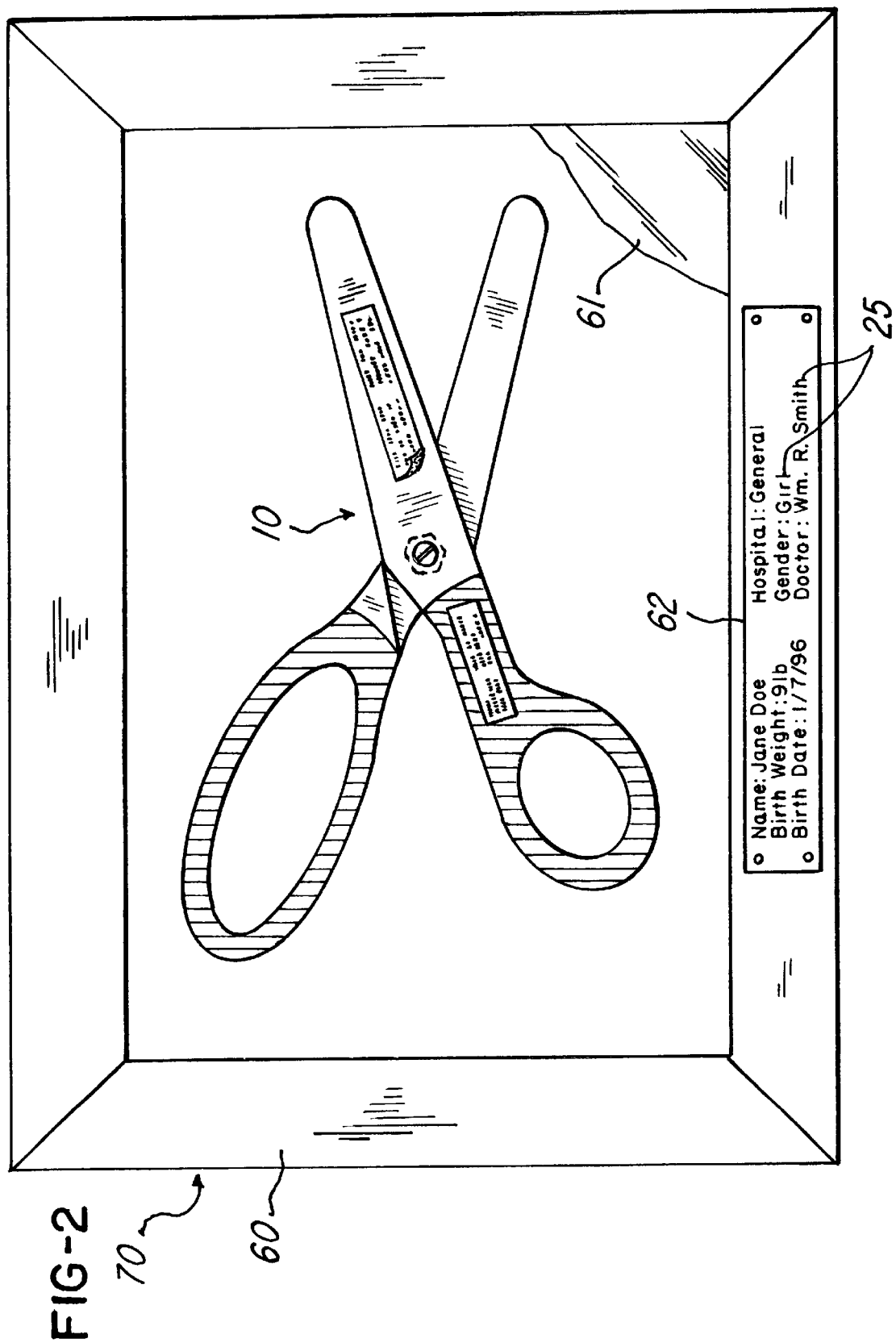
FIG. 2 is a view of the umbilical scissors shown in FIG. 1 showing the scissors mounted for display in a container or frame.

As best illustrated in FIG. 1, the scissors 10 comprise indicia 24 which may be associated with scissors 10 as shown. In the embodiment being described, the indicia 24 comprises a plurality of birth-related data 25, such as a baby's gender, name, weight, birthdate, hospital, birth time, doctor and the like. Further, the handles 20 and 22 may be integrally molded, covered, painted or the like to be colored coded to provide an indication of a baby's gender. For example, if a baby boy is delivered, the handles 20 and 22 may be covered, coated or painted blue or integrally molded with a blue material. Conversely, if the baby is a girl, the handles 20 and 22 may be covered, coated, painted or molded pink, as illustrated in FIGS. 1 and 2. Thus, it should be appreciated that while the scissors 10 in FIGS. 1 and 2 have been colored pink for illustration purposes, they could be covered, coated, painted or molded to comprise any color desired to indicate gender.

Further, if the baby to be delivered is unknown, a neutral color, such as green or yellow may be chosen. Alternatively, handle 20 may be colored blue while handle 22 is colored pink.

Although not shown, it is contemplated that a colored sheath or casing may be provided around part or all of the scissors 10 or around handles 20 and 22 to provide the color-coding and/or birth-related data indicia.

Notice that scissors 10 also comprise a plurality of label areas, such as areas 26 and 28, which may receive a label, such as a gummed label 30, which incorporates the birth data 25. Alternatively, the birth data 25 may be engraved or embossed directly into, for example, handle 22 (as shown in FIG. 1) or blade 14. As described later herein, if the birth data 25 is provided on a label, such as label 30, then it is placed on blade 14 after the scissors 10 have been used to sever the umbilical cord.

Referring now to FIG. 2, a scissor kit 70 is shown comprising a pair of scissors which are mounted for storage or display in a suitable container, such as the container defined by frame 60 and glass 61. Notice that the birth data 25 mentioned above may be situated on a label or plate 62 which, in turn, is situated. on frame 60 as shown.

After the scissors 10 are mounted in frame 60, the container may be hung on a wall or otherwise placed so as to store and display the scissors 10 and birth data 25.

Thus, the scissor kit 70 provides convenient means for memorializing birth data associated with the birth of a baby and providing means for permanently recording the birth-related data 25 using the very medical instrument that was used to sever the umbilical cord and separate the baby from its mother.

Advantageously, the apparatus and method of the present invention provide convenient means and method for recording and memorializing a birthing event and the data associated with the birth of a baby. The method and apparatus also provide suitable means for memorializing the umbilical severing event during the birthing process.

It should also be appreciated that if the birth data 25 is engraved directly on, for example, blade 14 or on packaging for the scissors 10, then the need for a label 30 may be eliminated. A method for recording the birth data will now be described.

Initially, during the birthing process, a baby is delivered (block 40 in FIG. 3). At decision block 42, it is determined whether or not the baby delivered at block 40 is a girl. If it is, then a pink handled pair of scissors can be selected at block 44. If it is not, then a blue pair of scissors is selected (block 46).

At block 48, the umbilical cord (not shown) is severed using the scissors selected at either block 44 or block 46.

At block 50, the scissors 10 are cleaned and then either engraved or labeled with the birth-related data 25 mentioned above (block 52). In this regard, the gummed label 30 may be generated to have the baby's name, weight, birthdate, hospital, birth time and doctor's name. The gummed label 30 is then placed or situated at area 26 on blade 14, as illustrated in FIG. 1.

At block 54, the scissors 10 may be situated or placed in a suitable package, such as the container defined by frame 60 and glass 61 in FIG. 2. Thereafter, the scissors 10 may be given or presented to the parents at block 56.

It should be appreciated that the framing at block 54 is optional and may be skipped so that the scissors 10 may be provided to parents without frame 60, rather than provided to the parents in frame 60.

At decision block 58, it is determined if another baby is to be delivered, and if there is, then the procedure loops back to block 40 as shown. Otherwise, the procedure is complete.

The scissors 10 may then be stored or displayed with the birth data 25 permanently affixed thereto. While the methods herein described, and the forms of apparatus for carrying these methods into effect, constitute preferred embodiments of this invention, it is to be understood that the invention is not limited to these precise methods and forms of apparatus, and that changes may be made in either without departing from the scope of the invention, which is defined in the appended claims.

I claim:

1. A method for recording birth data comprising the steps of:

providing a pair of birth data-indicating scissors suitable for severing an umbilical cord of a baby;

severing the umbilical cord with said pair of birth data-indicating scissors, recording birth data by labeling said birth data-indicating scissors with said birth data, including at least two of the following:

a baby's name, a birth date, a weight, a hospital, a doctor's name, or a gender.

2. The method as recited in claim 1 wherein said method further comprises the step of:

generating a label having birth data associated with the baby;

situating the label on the pair of birth data-indicating scissors.

3. The method as recited in claim 1 wherein said method further comprises the step of:

providing gender indicia integrally formed on said pair of birth data-indicating scissors.

4. The method as recited in claim 1 wherein said method further comprises the step of:

providing gender indicia in said handle, said gender indicia comprising a color.

5. The method as recited in claim 4 wherein said method further comprises the step of:

providing said color integrally formed in at least one handle of said pair of birth data-indicating scissors.

6. The method as recited in claim 5 wherein said color comprises blue for a baby boy or pink for a baby girl.

7. The method as recited in claim 1 wherein said method further comprises the step of:

providing gender indicia on said pair of birth data-indicating scissors.

8. The method as recited in claim 1 wherein said method further comprises the step of:

situating said birth data on a birth label;

placing said birth label on said pair of birth data-indicating scissors.

9. The method as recited in claim 1 wherein said method further comprises the step of:

situating said pair of birth data-indicating scissors in a container in order to display said scissors.

10. The method as recited in claim 1 wherein said method further comprises the step of:

framing said pair of birth data-indicating scissors in a frame.

\* \* \* \* \*